(12) United States Patent
Sugaya et al.

(10) Patent No.: US 8,791,128 B2
(45) Date of Patent: Jul. 29, 2014

(54) COMPOSITIONS FOR TREATING OR DELAYING THE ONSET OF HAIR LOSS

(75) Inventors: Kiminobu Sugaya, Winter Park, FL (US); Stephanie Merchant, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/061,159

(22) PCT Filed: Sep. 16, 2009

(86) PCT No.: PCT/US2009/057134
§ 371 (c)(1),
(2), (4) Date: Apr. 26, 2011

(87) PCT Pub. No.: WO2010/033576
PCT Pub. Date: Mar. 25, 2010

(65) Prior Publication Data
US 2011/0190320 A1    Aug. 4, 2011

Related U.S. Application Data

(60) Provisional application No. 61/097,443, filed on Sep. 16, 2008.

(51) Int. Cl.
A01N 43/90    (2006.01)
A61K 31/519    (2006.01)
C07D 487/04    (2006.01)
C07D 471/04    (2006.01)

(52) U.S. Cl.
CPC ............ *C07D 487/04* (2013.01); *C07D 471/04* (2013.01); *A61K 31/519* (2013.01)
USPC ..................................... 514/265.1

(58) Field of Classification Search
None
See application file for complete search history.

(56) References Cited

U.S. PATENT DOCUMENTS

| | | | |
|---|---|---|---|
| 4,959,368 A | 9/1990 | Awaya et al. | |
| 5,304,555 A | 4/1994 | Awaya | |
| 5,976,523 A | 11/1999 | Awaya | |
| 7,078,424 B2 | 7/2006 | Hamilton et al. | |
| 7,459,473 B2 | 12/2008 | Hamilton et al. | |
| 7,687,505 B2 | 3/2010 | Sugaya | |
| 7,951,811 B2 | 5/2011 | Nakazato et al. | |
| 8,106,194 B2 | 1/2012 | Nakazato et al. | |
| 8,273,756 B2 | 9/2012 | Sugaya et al. | |
| 2003/0113912 A1 | 6/2003 | Salito et al. | |
| 2003/0139410 A1 | 7/2003 | Sugaya et al. | |
| 2006/0003919 A1 | 1/2006 | Fortunel et al. | |
| 2006/0147435 A1 | 7/2006 | Moon et al. | |
| 2006/0257449 A1 | 11/2006 | Billy et al. | |
| 2007/0081963 A1 | 4/2007 | Oh et al. | |
| 2007/0270588 A1 | 11/2007 | Bischoff et al. | |
| 2008/0124306 A1 | 5/2008 | Sugaya | |

FOREIGN PATENT DOCUMENTS

| | | |
|---|---|---|
| JP | 2008325268 A | 12/1996 |
| JP | 2009295946 A | 11/1997 |
| JP | 2007204387 A | 8/2007 |
| WO | WO 0050568 | 8/2000 |
| WO | WO 0112236 | 2/2001 |
| WO | WO 03/060082 | 7/2003 |
| WO | WO 2005/040391 | 5/2005 |
| WO | WO 2006/009492 | 1/2006 |
| WO | WO 2006133876 | 12/2006 |

OTHER PUBLICATIONS

Sawaya et al. Novel agents for the treatment of alopecia. Seminars in Cutaneous Medicine and Surgery, vol. 17, No. 4. Dec. 1998: pp. 276-283.*
Ozeki et al. Promoted growth of murine hair follicles through controlled release of basic fibroblast growth factor. Tissue engineering. vol. 8, No. 3, 2002.*
Sanjo et al. A novel neurotrophic pyrimidine compound MS-818 enhances neurotrophic effects of basic fibroblast growth factor. Journal of Neuroscience Research, 54, 604-612, 1998.*
Madani et al. Alopecia areata update. J. Am. Acad. Dermatol. 2000; 42: 546-66.*
Lechner et al. "Stem/progenitor cells derived from adult tissues: potential for the treatment of diabetes mellitus", Am J Physiol Endocrinol Metab, Feb. 2003, 284:E259-E266, p. 264.
MS818, Annual Drug Data Report, Prous, Barcelona, ES, Jan. 1997, vol. 19, No. 3, p. 220.
Craven et al., "Clinical features of photodamaged human skin are associated with a reduction in Collagen VII", British Journal of Dermatology, 1997, vol. 137, pp. 344-350.
Dexter et al., "Stem cells in normal growth and disease", British Medical Journal, Nov. 1987, vol. 295, No. 6607, pp. 1192-1194.
Kanemura et al., "MS-818 Accelerates Mobilization of Endothelial Progenitor Cells and Differentiation to Endothelial Cells", Endothelium, 2004, vol. 11, pp. 221-230.
Musalmah et al., "Effect of vitamin E on plasma malondialdehyde, antioxidant enzyme levels and the rates of wound closures during wound healing in normal and diabetic rats", Asia Pacific Journal of Clinical Nutrition, Dec. 2002, vol. 11, s7, pp. 448-451.
Low et al., "Basic Fibroblast Growth Factor (FGF-2) Protects Rat Cochlear Hair Cells in Organotypical Culture From Aminoglycoside Injury", Journal of Cellular Physiology, 1996, vol. 167, pp. 443-450.
Yasuhara et al., "The Neurotrophic Pyrimidine Heterocyclic Compound MS-818 Promotes the Angiogenesis Induced by Basic FGF", Int. J. Clin. Pharm. Res, 1995, XV 5/6, pp. 167-174.

(Continued)

*Primary Examiner* — Anna Pagonakis
(74) *Attorney, Agent, or Firm* — Timothy H. Van Dyke; Beusse, Wolter, Sanks & Maire, P.A.

(57) ABSTRACT

Disclosed herein are novel methods and compositions for treating and/or preventing hair loss in patients. Specifically exemplified herein are compositions containing a modified pyrimidine that are topically applied to a scalp of an patient. Typically, the patient has androgenic alopecia, alopecia greata, postpartum alopecia or telogen effluvium.

3 Claims, 3 Drawing Sheets
(3 of 3 Drawing Sheet(s) Filed in Color)

(56) References Cited

OTHER PUBLICATIONS

Rosenquist et al., "Fibroblast Growth Factor Signalling in the Hair Growth Cycle: Expression of the Fibroblast Growth Factor Receptor and Ligand Genes in the Murine Hair Follicle", Development Dynamics, 1996, vol. 205, pp. 379-386.

Hebert et al. FGF5 as a regulator of the hair growth cycle: Evidence from targeted and spontaneous mutations:, Cell, 1994, vol. 78, issue 6, pp. 1017-1025.

Watanabe, et al., "A Neurotrophic Pyrimidine Compound, MS-818, Enhances EGF-Induced Restoration of Gastric Epithelial Wounds In Vitro", Journal of Clinical Gastroenterology, 1998, vol. 27, pp. S105-S109.

Both et al., "Liposome-encapsulated ursolic acid increases ceramides and collagen in human skin cells", Arch Dermatol Res, 2002, vol. 293, pp. 569-575.

Giangreco, et al., "Epidermal stem cells are retained in vivo throughout skin aging", Aging Cell, 2008, vol. 7, pp. 250-259.

Shimoda et al., "Effect of Heterocyclic Pyrimidine Compounds on UVB-Induced Cell Damage in Human Keratinocytes and on Melanogenesis in Mouse B16 Cells", Biol. Pharm. Bull, 2010, vol. 33, pp. 862-868.

Mitsuyama et al., "Role of a synthetic pyrimidine compound, MS-818, in reduction of infarct size and amelioration of sensorimotor dysfunction following permanent focal cerebral ischemia in rats", Journal of Neurosurgery, 2002, vol. 96 (6): pp. 1072-1076.

Beenken et al., "The FGF family: biology, pathophysiology and therapy", Nature Reviews, 2009, vol. 8, pp. 235-253.

Fathke, et al., "Contribution of Bone Marrow-Derived Cells to Skin: Collagen Deposition and Wound Repair", Stem Cells, 2004, vol. 22(5), pp. 812-822.

* cited by examiner

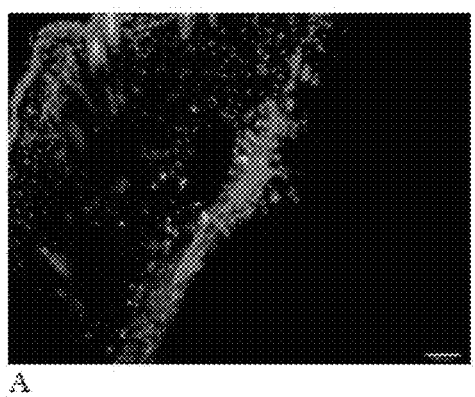
A
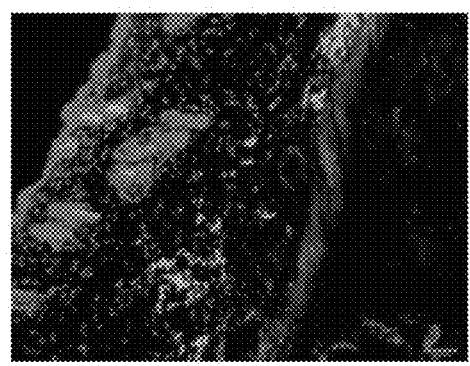
B
FIG. 3
FIG. 4
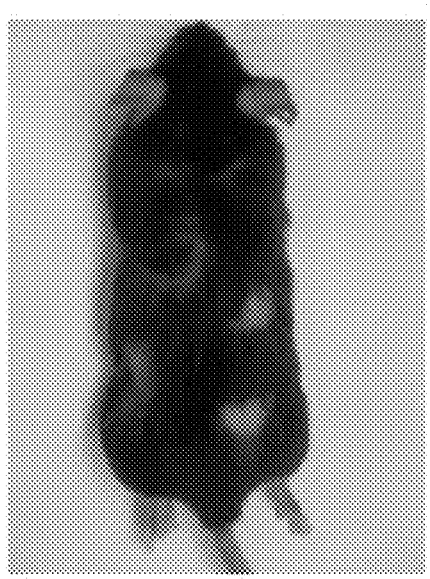
A
B
C
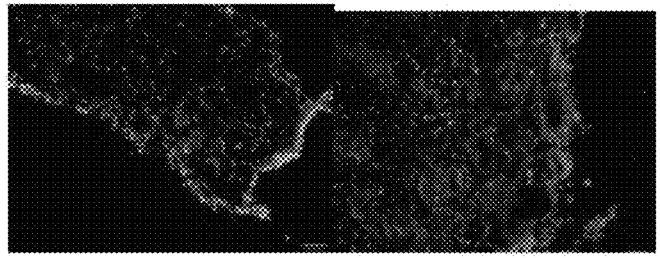
D          E

COMPOSITIONS FOR TREATING OR DELAYING THE ONSET OF HAIR LOSS

CROSS REFERENCE TO RELATED APPLICATIONS

This application is related to U.S. Provisional patent application No. 61/097,443; filed Sep. 16, 2008 to which priority is claimed under 35 USC 119. This provisional application is incorporated herein in its entirety.

BACKGROUND

Alopecia affects millions of men and women annually. 95% of all hair loss is caused by Androgenic Alopecia (a genetically inherited hair loss condition, otherwise known as pattern baldness). The remaining 5% of hair loss can be associated with a variety of health conditions, stress and trauma, diet and nutrition, environmental toxins, and medications. Currently, five out of 10 men and 21 million women will experience hair loss and the psychological affects associated with this condition. In the case of Androgenic Alopecia, testosterone is converted in the body to DHT (Di-hydrotesterone) by the enzyme 5AR (5 Alpha-deductase). DHT binds to specific points in the hair follicle called Androgen Receptor Sites (ARS) and this causes a mineralization which shrinks the diameter of the hair and reduces the time spent in the growth cycle, known as the anagen phase. Other known types of hair loss can be diagnosed as Telogen Effluvium, Traction or Traumatic Alopecia, Alopecia Areata, and Postpartum Alopecia. Telogen Effluvium produces a premature shedding of hair that is in resting or telogen phase. Causes of Telogen Effluvium can be contributed to illness, shock, and medication and can usually be reversed upon the removal of conditions. Traction or Traumatic Alopecia is demonstrated by patchy, scattered hair loss and is induced by heating elements used to dress hair or binding hair with bands; this is also reversible by removal of conditions. Alopecia Areata produces round irregular patchy spots of hair loss and the cause is unknown. But the commonality of all types of hair loss is the psychological effect it has on the men and women who experience these conditions.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 3. Immunohistochemistry: below A) control B) 3.0 mg/ml (circled area above in C where there is demonstrative hair re-growth.

FIG. 4: shows predominant hair re-growth (in white circle) in mouse #2 (A) using a topical application of 3.0 mg/ml. B) mouse prior to experiment. C) shaved area (in white circle) Below show immunohistochemistry of 3.0 mg/ml (D) where an overwhelming number of BrdU positive (green) cells coincides with the area of hair re-growth and 1.5 mg/ml (E) where proliferation is at an increase.

DETAILED DESCRIPTION

Figure 1:
FIG. 1 The pictures A-D are 20 uM sagittal sections of the dermal layer of mouse #1 A)Control (50% ETOH) at 10× B; stained with anti-BrdU (green) 1.5 mg/ml NBI-18 at 5× magnification; stained with anti-BrdU (green) and dapi (blue) C) 3.0 mg/ml NBI-18 at 10× magnification; stained with anti-BrdU (green) D) 3.0 mg/ml NBI-18 at 10× magnification; stained with anti-BrdU (green).
Figure 1:
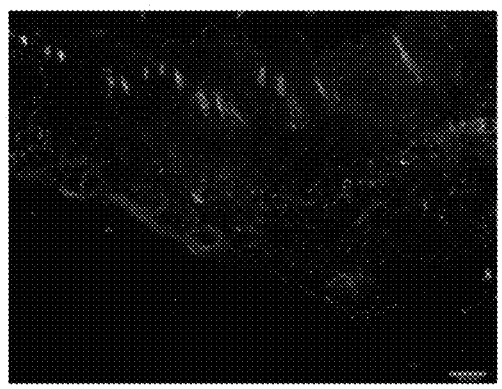
Figure 1:
Figure 1:
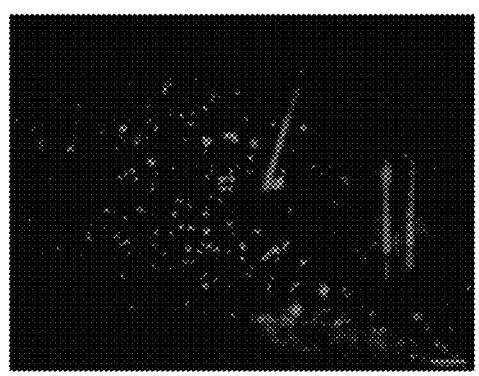

Recently, in the course of evaluating factors that influence stem cell proliferation, we made a provocative discovery. A heterocyclic pyrimidine molecule NBI-18 (2-piperadino-6-methyl-5-oxo-5,6-dihydro-(7H) pyrrolo-[3,4-d]pyrimidine maleate; Mwt. 349.54), previously described as having possible neurotrophic activity, can stimulate the proliferation of human NSCs in culture. The increase in proliferation was dose dependent in animal studies. We found that daily injections of NBI-18 for five days led to stable neurogenesis at four weeks in young and aged rodents alike. There were no discernible pathological effects, and no symptoms of toxicity due to the treatment with NBI-18 throughout the experiment. Based on these preliminary findings, we moved towards developing a topical application in an attempt to increase cell proliferation in a similar manner in relation to hair regeneration. C57 BL/6 mice were used to apply different concentrations of NBI-18 on shaved areas of skin with the incorporation of BrdU to detect cell proliferation, followed by immunohistochemistry. We were able to see an abundant increase in proliferating cells in all concentrations applied in comparison to the control area. More importantly, was the visibly complete hair growth that was in the treated areas compared to the non-treated areas. NBI-18 promises to be a novel compound leading to the development of regenerative therapeutics that can accelerate hair growth.

Recently, the inventors became intrigued by several reports suggesting that a family of heterocyclic pyrrolopyrimidine (PyP) compounds have a variety of growth promoting biological activities including increasing neurite outgrowth and repair of injured peripheral nerves and muscle. U.S. Pat. Nos. 4,959,368; 5,976,523. One derivative of interest is heterocyclic pyrimidine molecule referred to herein as 'NBI-18' (2-piperadino-6-methyl-5-oxo-5,6-dihydro-(7H) pyrrolo-[3,4-d]pyrimidine maleate; Mwt. 349.54). In other cell culture studies using neurons isolated from rodent cortex, NBI-18 was reported to be active primarily in the presence of various growth factors, including bFGF, nerve growth factor, EGF, and insulin-like growth factor. U.S. Patent Pub 20030139410. The mechanism of action of NBI-18 is not known, although some evidence implies the activation of the MAPK (mitogen activated protein kinase) pathway, a cascade that is also activated by peptide growth factors. It has been suggested that NBI-18 promoted the survival of rodent cortical neurons by reducing the rate of apoptosis, as measured by TUNEL assays. NBI-18 has been tested in isolated animal models—axon growth in mice and muscle regeneration in rats—with no evidence of mechanistic details relating to function. Mechanism of action studies to find the drug target, are planned as part of our ongoing research. Upon learning about the availability of NBI-18 family of molecules, it was hypothesized that the compounds may be involved in the proliferation process of Stem Cells and the inventors decided to examine the possible implication for genesis of Keratinocyte Stem Cells (KSCs) or possibly the human bulge cells which provide the niche for KSCs, in animal models. Early evidence from rodent studies, suggests that NBI-18 is absorbed well after intraperitoneal as well as oral administration and it has a t1/2>>4 h in rat circulation as shown by HPLC analysis. NBI-18 can be extracted 24 hours-post-injection from the epidermis of treated mice and the compound was not mutagenic, as indicated by a third party Ames test.

Based on the inventors' realizations, the decision was made to test NBI-18 in a topical application study to induce the genesis or re-growth of hair. Varying doses of NBI-18 [0.75 mg/ml, 1.5 mg/ml, 3.0 mg/ml, and control (50% ETOH)] was delivered in 5 ul drops to shaved locations on the back of C57 BL/6 mice. The varying doses were given 5 consecutive days and on day 4 and 5 BrdU (100 mg/kg, ip) was injected. Immunohistochemistry suggest a vast increase in Brdu+cells throughout the NBI-18 concentrations in comparison to the control, which didn't receive NBI-18. However, the most impressive data was the visible re-growth of hair in the treated areas, near to its original length within 7 days. The control or untreated areas showed no visible re-growth within the 7 day time frame. NBI-18 has proven to produce a desired affect in rodent models that show a predominant re-growth of hair using the topical application of the small molecular pyrimidine compound known as NBI-18. We are hypothesizing that NBI-18 treatment will lead to greater cytogenesis and eventually lead to a commercial product that will eradicate hair loss. These studies will be further described in the Examples provided below.

Accordingly, in one embodiment, the subject invention pertains to a method of increasing thickness of hair (i.e. number of hair fibers per surface area) and/or number hair follicles actively producing hair fibers in a human or nonhuman subject that comprises the administration of a hair-enhancing composition that contains a hair producing agent (HPA). U.S. Pat. No. 5,976,523 (523 patent) and U.S. Pat. No. 4,959,368 ('368 patent) teach a number of compounds that may be used as wound healing agents. The '523 patent teaches that the wound healing agents described therein act by potentiating growth factors and cytokines released in tissues as a result of injury or wounding of tissues. Essentially, the '523 patent teaches that the agents stimulate the migration of cells toward the wound. The present inventors have discovered that the same agents actually stimulate the proliferation of stem cells, which in turn, led to the discovery that the agents may be used in circumstances where tissues have not been wounded.

Accordingly, the agents presented in the '523 patent and '368 patent are incorporated herein by reference for disclosure of HPA agents. Also see U.S. Patent Pub 20080124306 Formulas 1 and 2 as set forth in the '523 patent are provided:

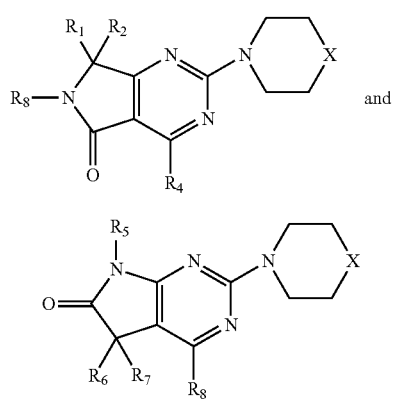

wherein $R_1$ to $R_8$ independently represent a hydrogen atom, a lower alkyl (especially $C_1$-$C_7$ alkyl) group, $CH_3OCH_2CH_2$—, —$CH_2CONH_2$, —$COCH_3$, —$COC_2H_5$ or —$CH_2OCOC_2H_5$, and X represents =NH, =N—$CH_3$, =N—$COCH_3$, =N—$COOC_2H_5$, =N—$SO_2CH_3$, =$CH_2$, =$CHCH_3$, =$CHC_2H_5$, —O— or —S— in which ph stands for a phenyl group.

Typical illustrative compounds of formula (1) include:
2-piperazino-6-methyl-5-oxo-5,6-dihydro(7H)pyrro-[3,4-d] pyrimidine,
2-(4-Methylpiperazino-6-methyl-5-oxo-5,6-dihydro-(7H) pyrro[3,4-d]pyrimidine,
2-(4-Ethylpiperazino-6-methyl-5-oxo-5,6-dihydro-(7H) pyrro[3,4-d]pyrimidine,
2-Piperidino-6-methyl-5-oxo-5,6-dihydro(7H)pyrro-[3,4-d] pyrimidine,
2-(4-Methylpiperidino)-6-methyl-5-oxo-5,6-dihydro(7H) pyrro[3,4-d]pyrimidine
2-(4-Ethylpiperidino)-6-methyl-5-oxo-5,6-dihydro-(7H) pyrro[3,4-d]pyrimidine
2-Morpholino-6-methyl-5-oxo-5,6-dihydro(7H)pyrro-[3,4-d]pyrimidine,
2-Thiomorpholino-6-methyl-5-oxo-5,6-dihydro(7H)-pyrro [3,4-d]pyrimidine,
2-piperazino-6-ethyl-5-oxo-5,6-dihydro(7H)pyrro-[3,4-d] pyrimidine,
2-piperazino-6-isopropyl-5-oxo-5,6-dihydro(7H)-pyrro[3,4-d]pyrimidine,
2-piperazino-6-n-butyl-5-oxo-5,6-dihydro(7H)-pyrro[3,4-d] pyrimidine,
2-piperazino-6-sec.-butyl-5-oxo-5,6-dihydro(7H)-pyrro[3, 4-d]pyrimidine,
2-piperazino-6-t-butyl-5-oxo-5,6-dihydro(7H)-pyrro[3,4-d] pyrimidine,
2-piperazino-4,6-dimethyl-5-oxo-5,6-dihydro(7H)-pyrro[3, 4-d]pyrimidine,
2-piperazino-6,7-dimethyl-5-oxo-5,6-dihydro(7H)-pyrro[3, 4-d]pyrimidine,
2-piperazino-6,7,7-trimethyl-5-oxo-5,6-dihydro-(7H)pyrro [3,4-d]pyrimidine,
2-Piperidino-4,6-dimethyl-5-oxo-5,6-dihydro(7H)-pyrro[3, 4-d]pyrimidine,
2-Piperidino-6,7,7-trimethyl-5-oxo-5,6-dihydro-(7H)pyrro [3,4-d]pyrimidine,
2-piperazino-7-methyl-6-ethyl-5-oxo-5,6-dihydro-(7H) pyrro[3,4-d]pyrimidine, and
2-piperazino-4-methyl-6-ethyl-5-oxo-5,6-dihydro-(7H) pyrro[3,4-d]pyrimidine.

Typical illustrative compounds of formula (2) include:
2-piperazino-7-methyl-6-oxo-5,6-dihydro(7H)pyrro-[2,3-d] pyrimidine,
2-(4-Methylpiperazino)-7-methyl-6-oxo-5,6-dihydro(7H) pyrro[2,3-d]pyrimidine
2-(4-Ethylpiperazino)-7-methyl-6-oxo-5,6-dihydro-(7H) pyrro[2,3-d]pyrimidine
2-(4-N-Acetylpiperazino)-7-methyl-6-oxo-5,6-dihydro(7H) pyrro[2,3-d]pyrimidine,
2-Piperidino-7-methyl-6-oxo-5,6-dihydro(7H)pyrro-[2,3-d] pyrimidine,
2-(4-Methylpiperidino)-7-methyl-6-oxo-5,6-dihydro(7H) pyrro[2,3-d]pyrimidine
4-(Ethylpiperidino)-7-methyl-6-oxo-5,6-dihydro-(7H)pyrro [2,3-d]pyrimidine,
2-Morpholino-7-methyl-6-oxo-5,6-dihydro(7H)pyrro-[2,3-d]pyrimidine,
2-Thiomorpholino-7-methyl-6-oxo-5,6-dihydro(7H)-pyrro [2,3-d]pyrimidine,
2-Piperidino-7-ethyl-6-oxo-5,6-dihydro(7H)pyrro-[2,3-d] pyrimidine, 2-Piperidino-7-n-propyl-6-oxo-5,6-dihydro(7H)-pyrro[2,3-d]pyrimidine,
2-Piperidino-7-isopropyl-6-oxo-5,6-dihydro(7H)-pyrro[2,3-d]pyrimidine,
2-Piperidino-7-n-butyl-6-oxo-5,6-dihydro(7H)-pyrro[2,3-d]pyrimidine,
2-Piperidino-7-t-butyl-6-oxo-5,6-dihydro(7H)-pyrro[2,3-d]pyrimidine,
2-Piperidino-5-methyl-6-oxo-5,6-dihydro(7H)pyrro-[2,3-d]pyrimidine,
2-piperazino-5-methyl-6-oxo-5,6-dihydro(7H)pyrro-[2,3-d]pyrimidine,
2-piperazino-4,7-dimethyl-6-oxo-5,6-dihydro(7H)-pyrro[2,3-d]pyrimidine,
2-Piperidino-5,7-dimethyl-6-oxo-5,6-dihydro(7H)-pyrro[2,3-d]pyrimidine,
2-Piperidino-5,5,7-trimethyl-6-oxo-5,6-dihydro-(7H)pyrro[2,3-d]pyrimidine,
2-piperazino-5,7-dimethyl-6-oxo-5,6-dihydro(7H)-pyrro[2,3-d]pyrimidine,
2-piperazino-5,5,7-trimethyl-6-oxo-5,6-dihydro-(7H)pyrro[2,3-d]pyrimidine,
2-Piperidino-4-methyl-7-ethyl-6-oxo-5,6-dihydro-(7H)pyrro[2,3-d]pyrimidine, and
2-Piperidino-5-methyl-7-ethyl-6-oxo-5,6-dihydro-(7H)pyrro[2,3-d]pyrimidine.

In certain embodiments the pyrimidine derivative of formula (1) is NBI-18, or 2-piperadino-6-methyl-5-oxo-5,6-dihydro(7H) pyrrolo[2,3-d]pyrimidine maleate (the $C_4H_4O_4$ maleate salt), as disclosed in U.S. Pat. No. 4,959,368, incorporated by reference herein. In certain in vivo embodiments, the pyrimidine derivatives of formulae (I) and (II) is administered at a concentration of between about 0.01 mg/kg/day to 50 mg/kg/day, more preferably between about 0.1 mg/kg/day to 10 mg/kg/day, even more preferably between about 1 mg/kg/day to 5 mg/kg/day, and even more preferably about 3 mg/kg/day. In these embodiments, the pyrimidine derivatives of formulae (I) and (II) is administered for between about 1 and 60 days, or more preferably between about 1 and 30 days, or more preferably between about 1 and 15 days, or even more preferably between about 1 and 10 days, or more preferably between about 2 and 7 days, or even more preferably about 5 days. In certain others of these embodiments, the methods further comprise the step of administering a growth factor. In certain embodiments, the growth factor comprises fibroblast growth factor, epidermal growth factor or a combination thereof.

Pharmaceutical compositions comprising the active compounds of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically. The actual pharmaceutical composition administered will depend upon the mode of administration. Virtually any mode of administration may be used, including, for example topical, oral, systemic, inhalation, injection, transdermal, etc.

The active compound may be formulated in the pharmaceutical compositions per se, or in the form of a pharmaceutically acceptable salt. As used herein, the expression "pharmaceutically acceptable salt" means those salts which retain substantially the biological effectiveness and properties of the active compound and which is not biologically or otherwise undesirable. Such salts may be prepared from inorganic and organic acids and bases, as is well-known in the art. Typically, such salts are more soluble in aqueous solutions than the corresponding free acids and bases.

For topical administration, the active compound(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets, chewing gum or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For administration by inhalation, the active compound(s) can be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For prolonged delivery, the active compound(s) can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compounds(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

EXAMPLE 1

Preparation of NBI-18 Composition

In preliminary studies, the inventors found that NBI-18 injections (5 mg/kg) increased proliferation of cells in the brain of rodents. In this study, the inventors determined a dose range where keratinogenesis occurs in healthy mice to help us learn about the fate of newly formed cells within the epidermis. This data enables selection of a relevant dose range for treating hair loss conditions such as Androgenic Alopecia, Alopecia Areata, Postpartum Alopecia and Telogen Effluvium using a topical application. Normal healthy C57 BL/6 mice exhibiting natural active behavior were used to test the topical application of NBI-18. In order for us to eliminate unnecessary anesthesia, our vehicle of delivery was 50% Ethanol (ETOH). NBI-18 was suspended in 50% ETOH using the concentrations of 0.75 mg/ml, 1.5 mg/ml, 3.0 mg/ml, and control (50% ETOH) respectively.

Results. In using 50% ETOH as our delivery vehicle we were able to demonstrate through immunohistochemistry, an increased population in BrdU positive stained cells. This visible increase was incurred in all concentrations of NBI-18 and showed a dramatic elevation in BrdU positive stained cells in comparison to the control which received just 50% ETOH. Although the elevations in BrdU positive stained cells did not demonstrate a dose dependent increase as one would expect, this could be due to the probability of that each recurring application was not placed in exactly the same area on some of the mice. A more applicable delivery system will be developed in future studies.

EXAMPLE 2

Toxicity Study

A total of 16 male C57 BL/6 mice (12 weeks old) weighing 25-30 g were used to investigate the toxicity of NBI-18. The mice were maintained on a 12-h light/dark cycle, and had free access to food and water through the study period. These animals were housed four per cage. In this study, animals were divided into four groups (four/group). Acute toxicity has been tested up to 1000 mg/kg. NBI-18 (0, 100, 300,1000 mg/kg/day, i.p.) was injected for 7 days and for the control group, the same volume of vehicle saline was injected. Bromodeoxyuridine (BrdU)(Sigma Chemical Co., St Louis, Mo.), was injected (100 mg/kg/day, i.p.) for the last three days (days 5-7). For behavioral testing, rotarod and open field tests were used to examine balance and coordination of mice before, during and after NBI-18 injection. Also, postural reflex and forelimb placing tests were performed to evaluate the neurological functions for the animals. All the animals were anesthetized with pentobarbital (i.p.) 48 h after the last BrdU injection and immediately per fused with 4% paraformaldehyde fixative. The brains were immediately dissected, post fixed for 24 h and processed for immunohistochemistry.

Results. The animals demonstrated no immediate behavioral or neurological changes in the study. They showed no symptoms of toxicity due to the treatment with NBI-18 throughout the experiment. An Ames was conducted by a third party company and the results were consistent showing no mutagenesis or toxicity, suggesting that NBI-18 is safe and won't have any adverse effects on the mice.

EXAMPLE 3

In Vivo Study

A. Two C57 BL/6 mice were selected for the topical application study of NBI-18. The mice were prepped by shaving four specific locations lateral/dorsal in a circular pattern. NBI-18 was delivered to the specified areas (right, counterclockwise from lowest to highest dose, then control) in concentrations of 1.5 mg/ml, 3.0 mg/ml, 6.0 mg/ml and control (50% ETOH) respectively. The solutions were applied to the center of these locations in a 5 ul dose for 5 consecutive days and on days 4 and 5 BrdU (100 mg/K, ip) was injected. On day 7 the mice were euthanized using a high dose pentobarbital (70 mg/kg, ip) and the treated epidermis was dissected and placed into 4% paraformaldehyde fixative for 48 hour Immunohistochemistry of epidermis. Epidermal sections were mounted into square embedding molds with freezing medium (O.C.T. compound, Tissue Tek), sliced in 20 uM sections then mounted onto adhesive coated slides (Instrumedics, Inc) via tape transfer method. Slides were washed with PBS then placed in 2NHCL for 30 minutes to induce histone release. Slides were then washed again with PBS, then blocked using 3% Donkey serum in PBST for 1 hour. Primary anti-body suspended in blocking solution used was anti-BrdU (sigma) at 1:1000 overnight in 4C. Slide were washed 3× then placed in secondary anti-body suspended in blocking solution, FITC (Jackson ImmunoResearch) at 1:500 for 2 hours at room temperature then washed with PBS. Slides were mounted using Vectashield with Dapi. Photographs were taken using an inverted fluorescent microscope (Leica, DMI 6000 B with Q-imaging Retiga exi camera).

Results. The Control (A) show a much reduced level of BrdU signaling along with a nonmigration pattern; the new cells are sporadic throughout the tissue sample. All of the NBI-18 treated samples (B-D) showed mass increases of newly developed cells but most importantly they demonstrated an alignment towards migration patterns. FIG. 1.

B. Four C57 BL/6 mice were selected for the topical application study of NBI-18. The mice were prepped by shaving four specific locations lateral/dorsal in a circular pattern. NBI-18 was delivered to the specified areas (right, counter-clockwise from lowest to highest dose, then control) in concentrations of 0.75 mg/ml, 1.5 mg/ml, and 3.0 mg/ml, and control (50% ETOH) respectively. The solutions were applied to the center of these locations in a 5 ul dose for 5 consecutive days and on days 4 and 5 BrdU (100 mg/K, ip) was injected. On day 7 the mice were euthanized using a high dose pentobarbital (70 mg/kg, ip) and the treated epidermis was dissected and placed into 4% paraformaldehyde fixative for 48 hour.

Immunohistochemistry of epidermis. Epidermal sections were mounted into square embedding molds with freezing medium (O.C.T. compound, Tissue Tek), sliced in 20 uM sections then mounted onto adhesive coated slides (Instru-medics, Inc) via tape transfer method. Slides were washed with PBS then placed in 2N HCL for 30 minutes to induce histone release. Slides were then washed again with PBS, then blocked using 3% Donkey serum in PBST for 1 hour. Primary anti-body suspended in blocking solution used was anti-BrdU (sigma) at 1:1000 overnight in 4C. Slide were washed 3× then placed in secondary anti-body suspended in blocking solution, FITC (Jackson ImmunoResearch) at 1:500 for 2 hours at room temperature then washed with PBS. Slides were mounted using Vectashield with Dapi. Photographs were taken using an inverted fluorescent microscope (Leica, DMI 6000 B with Q-imaging Retiga exi camera).

Figure 2:
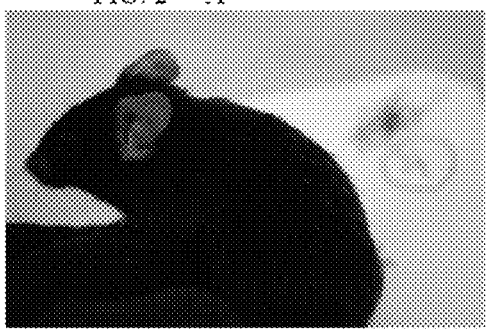
FIG. 2 Pictures A-C are all of mouse #4. A) Prior to experiment (nothing has been done to the animal. B) The circled area shows where the hair has been shaved and what appears to look like a water drop is the application of solutions prior to evaporation (this picture was taken on the first day of application). C) The circled area shows where there was a predominant re-growth of hair.
Figure 2:
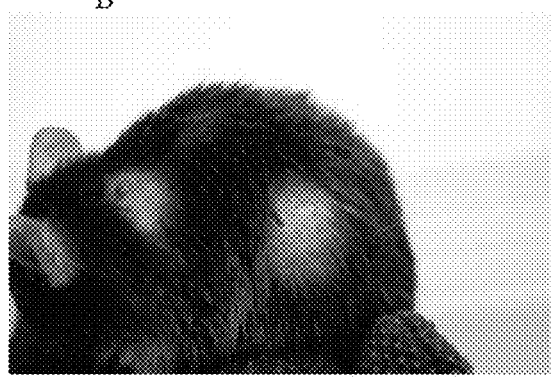
Figure 2:
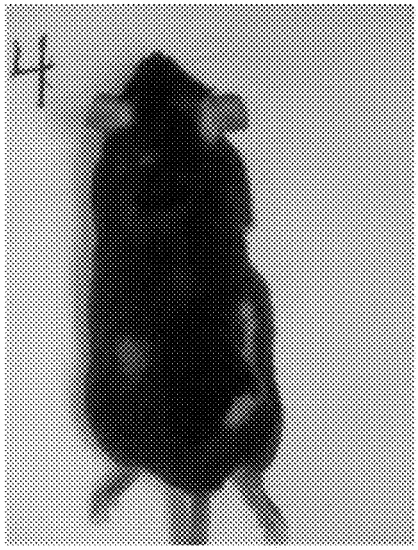

Results. In all of the mice there were some varying levels of increase in BrdU positive cells in comparison with the controls as shown in the immunohistochemistry. FIG. 3. However the most visible effect is the actual hair re-growth demonstrated in the pictures of the mice. FIG. 2 (mouse 4) and FIG. 4 (mouse 2). Even though the locations of hair re-growth occur sporadically throughout the three concentrations of NBI-18 (0.75 mg/ml, 1.5 mg/ml, 3.0 mg/ml.), there is absolutely no visible hair regeneration in the controls within the same time constraints. This can be explained by the probability of each recurring applications ability was placed in exactly the same area. A 5 ul drop onto the back of a moving mouse allows for a possible missed location involving topical applications. However, the data clearly demonstrates the differences between the control and compound. A next feasible step will be to test this compounds efficacy against similar proven compounds such as minoxidil (Rogaine).

Discussion related to Examples 1-3. Preliminary studies have shown that NBI-18 increases the number of BrdU positive cells in mice that have received a 5 day consecutive topical application of 5 ul doses of 0.75 mg/ml, 1.5 mg/ml, 3.0 mg/ml and 50% ETOH (control). There are three cycles of hair growth; the anagen phase (the growing phase), the catagen phase (where hair stops growing) and the Telogen phase (which is the resting phase). The anagen phase last for appx.1000 days but can range from 2-6 years and it is considered the "on" phase or growing phase. The catagen phase lasts for only 1-2 weeks and during this phase the hair follicle shrinks and starts to die; this is known as the transitional phase. Telogen is the final phase often referred to as the "resting" or "off" phase and this is when the hair follicle renews or activates itself and a new hair in the anagen phase develops pushing the old hair out. The mechanistic effect of NBI-18 has on the stem cell population and how it directly effects the hair follicles is still in the process of being elucidated. However, another study using the monoxidil showed that in animal studies, topical minoxidil shortens the telogen phase, causing premature entry of new hair from resting hair follicles into anagen phase, thus producing a mechanistic blocking effect of the natural pathways. In order to preserve this mechanistic effect, the delivery dosage must continually be maintained. In comparison our compound works on the physiological pathway of the stem cell environment by increasing the proliferation of endogenous cells. Once this increase is achieved, usually within a 3-5 day treatment schedule there is no need to continue using the compound.

The small molecule NBI-18 bypasses the ethical and technical issues associated with stem cell transplantation by directly coaxing the production of healthy new endogenous cells. NBI-18 and its variants represent a unique class of synthetic heterocyclic compounds that are stable, orally bioavailability, and easily manufactured. The inventors are able to use a compound that works synergistically with natural stem cell growth factors to speed up cell proliferation. Such compounds are a rare and valuable therapeutic candidate. This idea delivers an exciting time for everyone. It is a new and innovative drug that could change the aesthetics of people everywhere. The adverse psychological effects caused hair loss will no longer be an in issue in both men and women.

The disclosures of all cited patent documents, publications and references are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A method of inducing hair growth in a patient having hair follicles comprising administering a therapeutically effective amount of an hair producing (HPA) to said patient, wherein said HPA is 2-Piperazino-6-methyl-5-oxo-5,6-dihydro(7H)pyrro-[3,4-d]pyrimidine, or a pharmaceutically acceptable salt thereof, and wherein said administering is topical administration.

2. The method of claim 1, wherein said HPA is in a composition further comprising a pharmaceutically acceptable carrier.

3. The method of claim 2, wherein said composition is a solution, gel, ointment, cream or suspension.

* * * * *